United States Patent
Kim

(10) Patent No.: US 7,335,612 B2
(45) Date of Patent: Feb. 26, 2008

(54) MESH COTTON WITH SEPARATING NET AND METHOD FOR ITS MANUFACTURING

(76) Inventor: Tack-Young Kim, 19-5 Gian-Ri, Tacan-Eup, Hwaseong-Shi, Kyungki-Do (KR)

(*) Notice: Subject to any disclaimer, the term of this patent is extended or adjusted under 35 U.S.C. 154(b) by 219 days.

(21) Appl. No.: 10/544,872

(22) PCT Filed: Jul. 23, 2004

(86) PCT No.: PCT/KR2004/001862

§ 371 (c)(1),
(2), (4) Date: Aug. 9, 2005

(87) PCT Pub. No.: WO2005/051440

PCT Pub. Date: Jun. 9, 2005

(65) Prior Publication Data

US 2006/0148348 A1    Jul. 6, 2006

(30) Foreign Application Priority Data

Nov. 25, 2003   (KR) ............... 10-2003-0083978

(51) Int. Cl.
*B32B 3/00* (2006.01)
*A61F 13/00* (2006.01)

(52) U.S. Cl. ............ 442/59; 442/1; 442/102; 101/3.1; 602/42; 602/43

(58) Field of Classification Search ........... 602/41–43, 602/75–79; 442/159, 1, 102; 101/3.1
See application file for complete search history.

(56) References Cited

U.S. PATENT DOCUMENTS

| | | | |
|---|---|---|---|
| 3,552,994 A * | 1/1971 | Dipner ................. | 442/45 |
| 4,616,644 A | 10/1986 | Saferstein et al. | |
| 4,995,382 A | 2/1991 | Lang et al. | |
| 5,328,450 A | 7/1994 | Smith et al. | |
| 5,681,579 A | 10/1997 | Freeman | |
| 5,990,377 A | 11/1999 | Chen et al. | |
| 2002/0032421 A1 | 3/2002 | Scott, Jr. et al. | |

FOREIGN PATENT DOCUMENTS

KR    1020040005217    1/2004

* cited by examiner

*Primary Examiner*—Kim M Lewis
(74) *Attorney, Agent, or Firm*—IPLA P.A.; James E. Bame

(57) ABSTRACT

Disclosed are a mesh cotton with a separating net on a surface thereof and a method of manufacturing the same. The mesh cotton (10) is manufactured by layering a plurality of cotton sheets (13) and adhering the layered cotton sheets to each other with an acryl binder, embossing a surface of the layered cotton sheets, and forming a transparent mesh-type separating net (11) using a dilution of a mixture of ethylene copolymers on an outer surface of the layered cotton sheets. The separating net is also formed by applying in a mesh form a dilution of a mixture of a wax or a paraffin and the mixture of ethylene copolymers to an outer surface of the layered mesh cotton, and solidifying the dilution. The separating net may further include an antioxidant and other additives. The mesh cotton is completely removed from applied wound sites by the separating net, and maintains elasticity while the layered cotton sheets are not easily separated from each other.

12 Claims, 6 Drawing Sheets

MESH COTTON WITH SEPARATING NET AND METHOD FOR ITS MANUFACTURING

TECHNICAL FIELD

The present invention relates, in general, to a medical mesh cotton being applicable to wound sites. More particularly, the present invention relates to a mesh cotton with a separating net on a surface thereof to allow easy removal thereof from wound sites, and a method of manufacturing such a mesh cotton.

BACKGROUND ART

Medical gauzes are typically prepared by weaving a bleached cotton yarn or hot-compressing absorbent cotton sheets containing a viscose short staple fiber with a porous polymer film. The woven cotton gauzes have disadvantages of requiring a complex manufacturing process and not being easily removed from wound sites, thus causing pain to patients upon removal.

Gauzes made of only absorbent cotton reduce patients' discomfort and utilize the excellent absorbing ability of cotton. However, due to its property of adhering to wound sites, absorbent cotton is difficult to detach from the wound site. Also, since gauzes made only of cotton have weak tension, to overcome this weakness, it is wrapped with a woven or non-woven fabric to form a double-layered structure. On the other hand, gauzes manufactured by hot compression of absorbent cotton containing a viscose short staple fiber with a porous polymer film are easily removed from wound sites, but are problematic in terms of having low absorption ability, causing psychological stress in received patients, and generating static electricity.

These problems can be solved by a mesh cotton disclosed in Korean Pat. Application No. 1020020039703 submitted by the present applicant and titled "Mesh cotton with mesh-type net integrated with surface thereof into a single body and method of manufacturing the same". The mesh cotton disclosed in the Korean patent application submitted by the present applicant is prepared by alternately layering cotton sheets containing an adhesive resin that melts at low temperature, for example, by a spray method after being defatted, and pure cotton sheets not treated with any compound after being defatted, forming a mesh-type net on a surface of multi-layered cotton sheets, and subjecting the multi-layered cotton to hot compression. During the hot compression, the adhesive resin is melted, leading to integration of the multi-layered cotton sheets with the meshed net formed on the surface thereof into a single body.

However, in the conventional mesh cotton, the mesh structure is often destroyed during hot compression. Thus, the conventional mesh cotton, although a mesh structure is formed on a surface thereof, is not easy to completely remove from applied wound sites. Also, in this case, separations occur between the multi-layered cotton sheets attached to each other with the adhesive resin. If a stronger adhesive resin is used to prevent the multi-layered cotton sheets from being separated from each other, the resulting mesh cotton has low elasticity and is thus hard.

DISCLOSURE

Technical Problem

Figure 1:
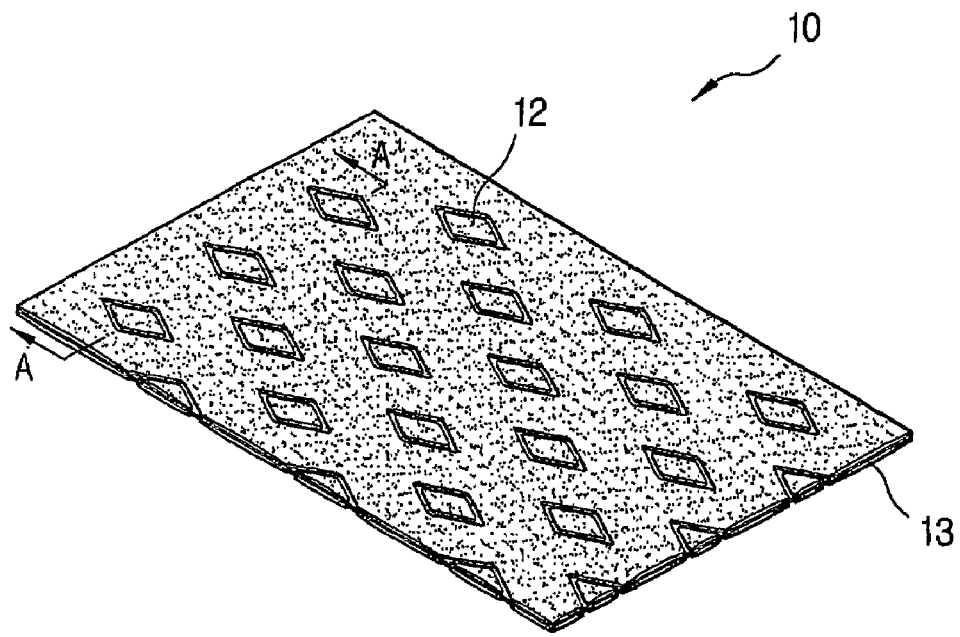
FIG. 1 is a perspective view of a mesh cotton according to an embodiment of the present invention.

Accordingly, the present invention has been made keeping in mind the above problems occurring in the prior art, and an object of the present invention is to provide a mesh cotton which is completely removed from applied wound sites and composed of layered cotton sheets being not easily separated from each other while maintaining good elasticity.

Best Mode

To accomplish the above objects, the present invention provides a mesh cotton with a separating net on a surface thereof. The mesh cotton is characterized by being manufactured by layering a plurality of cotton sheets and adhering the layered cotton sheets to each other using an acryl binder, forming a transparent mesh-type separating net on an outer surface of the layered cotton sheets using a dilution of a mixture of ethylene copolymers, and embossing an outer surface of the layered cotton sheets to form embossments.

In the present invention, to further facilitate the removal of the mesh cotton from applied wound sites, the separating net is formed by applying in a mesh form a dilution of a mixture of a wax and the mixture of ethylene copolymers, or a dilution of a mixture of a paraffin and the mixture of ethylene copolymers, to the outer surface of the layered mesh cotton, and solidifying the dilution.

In addition, the present invention provides a method of manufacturing a mesh cotton with a separating net on a surface thereof, comprising: layering a plurality of cotton sheets and adhering the layered cotton sheets to each other; forming a mesh-type separating net on an outer surface of the layered adhered cotton sheets using a mixture of ethylene copolymers; embossing an outer surface of the cotton sheets by heating under pressure to form embossments; and sectioning the embossed cotton sheets into a predetermined size and shape. If desired, the embossing of the cotton sheets may be carried out before the forming of the separating net. The layering and adhering of the cotton sheets is carried out by homogeneously mixing the cotton sheets with a viscose short staple fiber, multi-layering the cotton sheets and compressing the multi-layered cotton sheets using a roller. Alternatively, the layering and adhering of the cotton sheets is carried out by layering the plurality of cotton sheets and adhering the layered cotton sheets to each other using an acryl binder.

In case of adhering the cotton sheets using an acryl binder, the layering and adhering of the cotton sheets comprises: layering the plurality of cotton sheets with a roller; and adhering the layered cotton sheets to each other by spraying the acryl binder onto a surface of the layered cotton sheets and absorbing the acryl binder at the opposite surface of the layered cotton sheets, wherein the layered cotton sheets are dried after the layering and adhering of the cotton sheets. In the present method, the forming of the mesh-type separating net comprises: printing the mixture of ethylene copolymers or a wax or a paraffin dissolved in the mixture of ethylene copolymers onto the outer surface of the layered adhered cotton sheets to provide the mesh-type separating net; and drying the printed separating net.

The printing of the mesh-type separating net comprises partially applying the mixture of ethylene copolymers, contained in a plurality of depressions on an outer embossed surface of a printing roller with a lattice-shaped mesh structure on the outer embossed surface, to the outer surface of the layered cotton sheets. The embossing of the cotton sheets comprises passing the layered cotton sheets between a pair of embossing rollers with an outer uneven surface to emboss both surfaces of the layered cotton sheets by the uneven surfaces of the embossing rollers.

Preferred embodiments of the present invention will be described below with reference to the accompanying drawings. The same reference numerals are used throughout the different drawings to designate the same or similar components.

Figure 2:
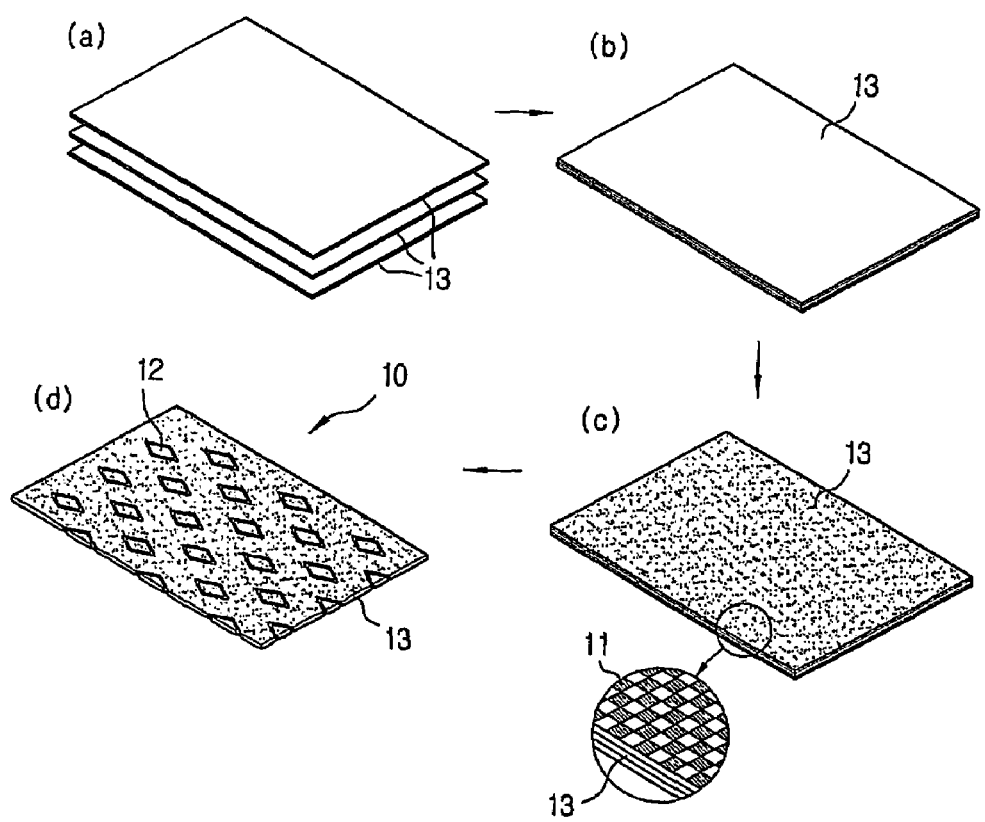
FIG. 2 shows a process of manufacturing the mesh cotton of FIG. 1.
Figure 3:
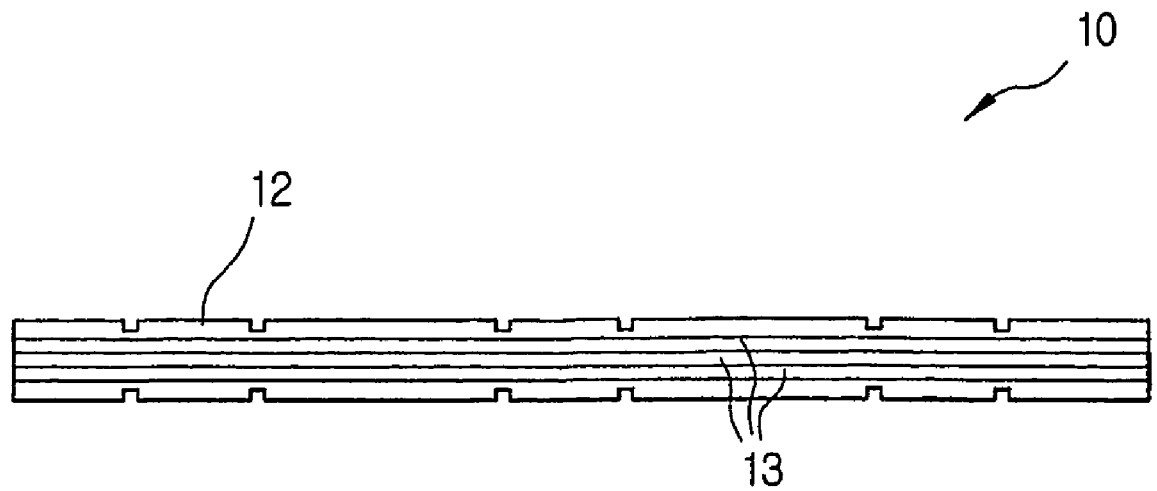
FIG. 3 is a sectional view taken along the line A-A' of FIG. 1.

FIG. 1 is a perspective view of a mesh cotton according to an embodiment of the present invention, and FIG. 2 is a sectional view taken along the line A-A' of FIG. 1.

As shown in the figures, a mesh cotton according to the present invention has a predetermined shape with a predetermined size by a sectioning process. In the manufacture of the mesh cotton 10, first, a plurality of cotton sheets are layered and adhered to each other by an acryl binder. A mesh-type separating net 11 is provided on both surfaces of the layered cotton sheets by a dilution of a mixture of ethylene copolymers. As shown in the figures, the mesh-type separating net 11 is applied not to the whole but to a portion of each of both surfaces of the layered cotton sheets by a printing method. The separating net 11 may be printed in a variety of forms, such as lattice, dot or line patterns 12.

Since the separating net 11 is composed of the mixture of ethylene copolymers that are not harmful to the body, it does not adhere to the skin of patients. The separating net 11 is formed using the mixture of ethylene copolymers alone, or, to further facilitate the removal of the mesh cotton of the present invention from applied wound sites, using a wax, a paraffin or other additives diluted with the mixture of ethylene copolymers. The separating net 11 has a very small mesh size and a fine thickness, which are indistinguishable with the naked eye.

As shown in the figures, embossments are formed on an outer surface of the mesh cotton 10. The embossments are formed by employing a pair of embossing rollers 60 with an outer uneven surface. The embossments allow the mesh cotton 10 to maintain constant elasticity and facilitate the removal of the mesh cotton 10 from wound sites of patients.

With reference to FIGS. 3 to 6, the method of manufacturing the mesh cotton 10 according to the present invention will be described in detail below.

Figure 4:
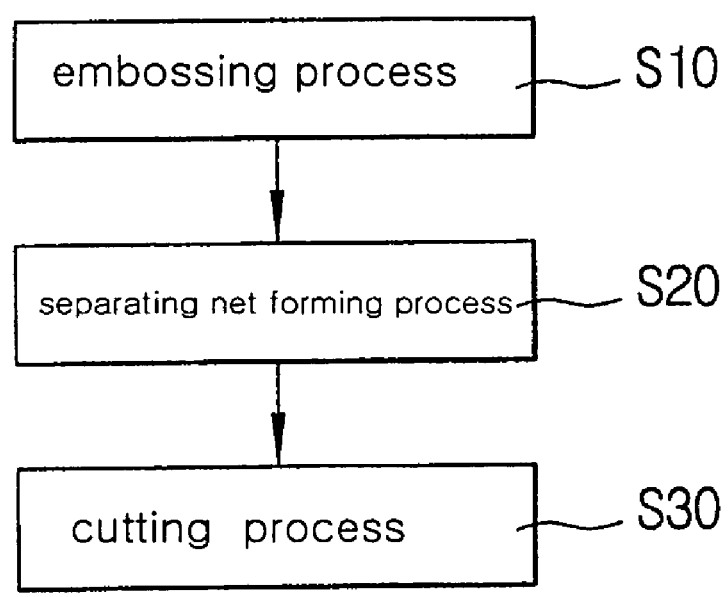
FIG. 4 is a flow chart of a process of manufacturing a mesh cotton.
Figure 5:
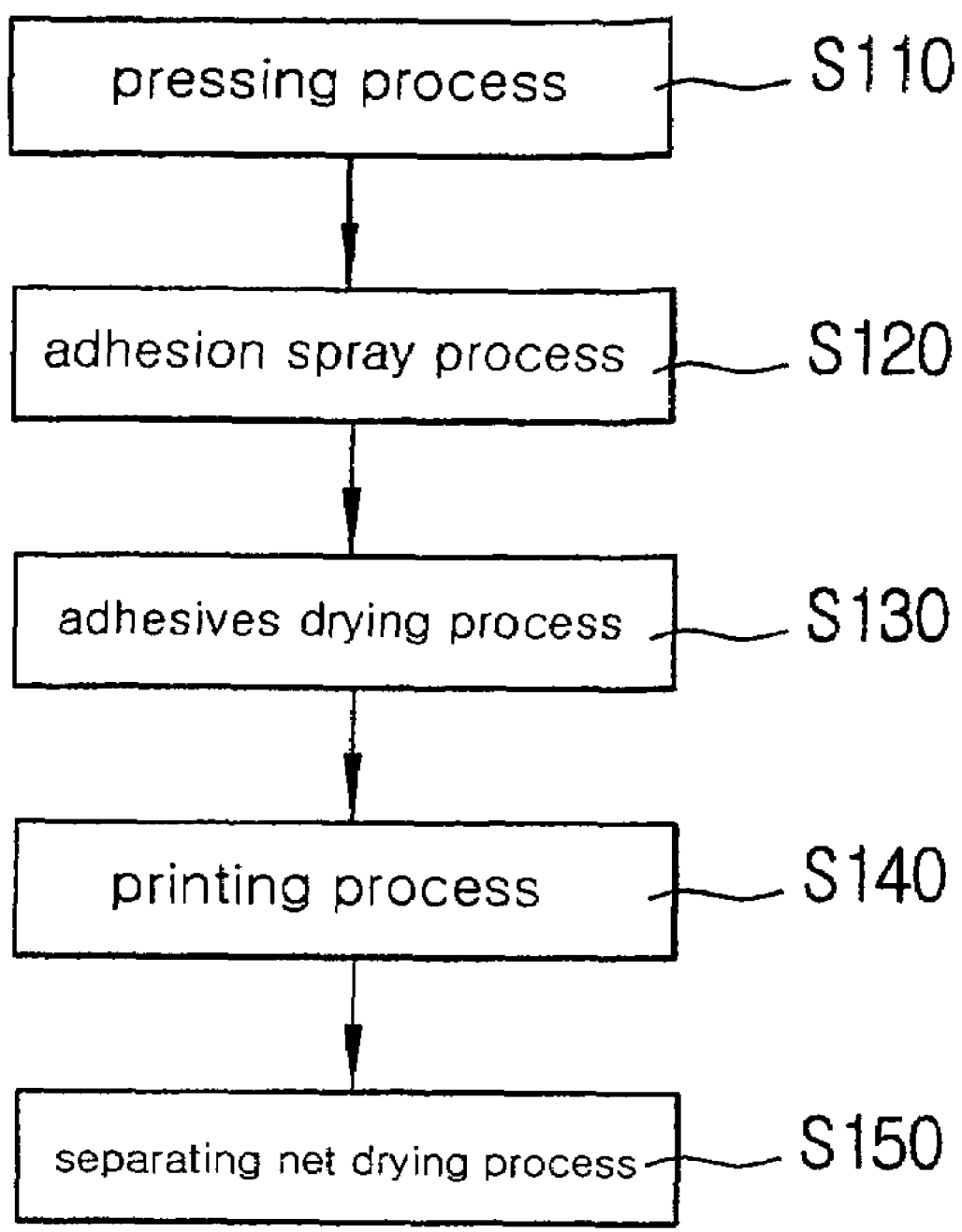
FIG. 5 is a flow chart of a process of forming a separating net of FIG. 4.

As shown in FIG. 4, the mesh cotton of the present invention is manufactured by a process including steps of embossing cotton sheets (S10), forming a separating net on the cotton sheets 13 using a dilution of a mixture of ethylene copolymers (S20), and sectioning the resulting cotton sheets into a predetermined size (S30). If desired, the step of forming a separating net is carried out before the embossing step. As shown in FIG. 4, the step (S20) of forming the separating net includes layering and compressing a plurality of cotton sheets (S110), adhering the layered cotton sheets at a compressed state to each other by spraying an adhesive (S120) thereinto, drying the sprayed adhesive (S130), printing a mesh-type separating net onto a surface of the adhered cotton sheets (S140), and drying the formed separating net (S150).

With reference to FIGS. 6 to 9, the above-mentioned process will be described in more detail below.

Figure 6:
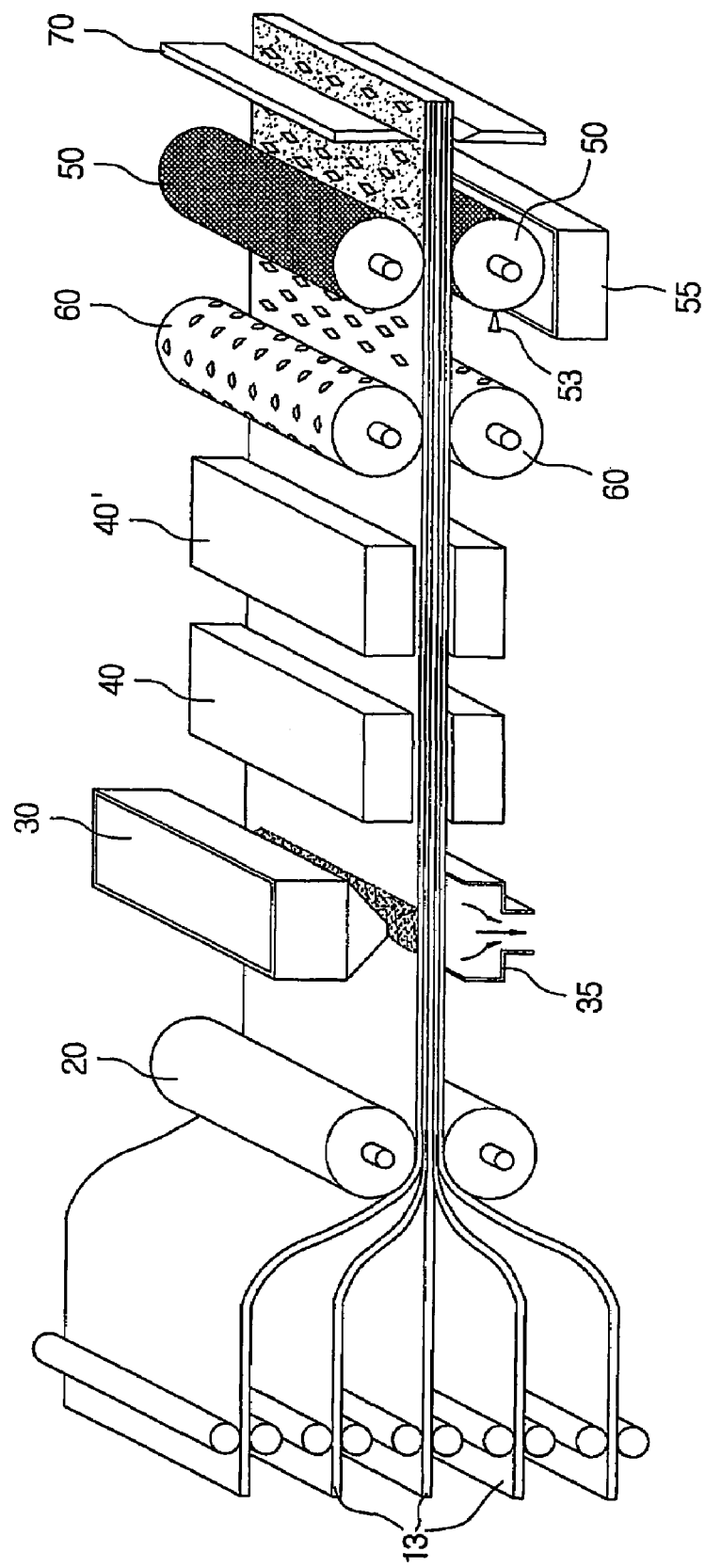
FIG. 6 is a view for describing an embodiment of the process of FIG. 4.

A plurality of cotton sheets is layered by compression using a roller 20, and the layered cotton sheets pass below a sprayer 30 that sprays an acryl binder downwardly. As shown in FIG. 6, the sprayer 30 located above the cotton sheets sprays the acryl binder through a nozzle, and the fog-like sprayed acryl binder that passes through the layered cotton sheets is absorbed by an absorber 35 located below the cotton sheets. Since, by virtue of this constitution, the acryl binder sprayed by the upper sprayer 30 goes through the layered cotton sheets and is absorbed by the absorber 35 beneath, it is evenly distributed in the layered cotton sheets. If desired, the acryl binder is sprayed onto both surfaces of the layered cotton sheets by turning the layered cotton sheets upside down or changing a location of the sprayer and the absorber. When passing through a dryer 40, the acryl binder evenly distributed in the layered cotton sheets is solidified, causing the cotton sheets to adhere to each other. In addition, if desired, the process further includes hardening the acryl binder at high temperature.

Thereafter, the layered cotton sheets are embossed. If desired, the embossing of the layered cotton sheets is carried out after the formation of the separating net. The embossing of the layered cotton sheets is achieved by employing a pair of embossing rollers 60 having an outer uneven surface 61. That is, the layered cotton sheets are embossed when passing between the pair of embossing rollers 60 (see, FIG. 9).

After being adhered to each other and embossed, the layered cotton sheets pass between a pair of printing rollers 50 to form the mesh-type separating net 11 on a surface thereof. The printing rollers 50 have a plurality of depressions 51 provided on their surfaces to form a mesh shape as shown in an enlargement of FIG. 2. That is, the printing rollers 50 have small-sized rectangular depressions and embossments that are alternatively formed thereon (see, FIG. 8). The printing rollers 50 are not entirely coated with a dilution 54 of the mixture of ethylene copolymers. Instead, the dilution 54 is stored in the depressions 51 and printed onto the layered cotton sheets. To accomplish partial printing, the dilution 54 present on the roller's surface except for sites of the depressions 51 is removed by a blade 53. The lower printing roller 50 rotates while a portion thereof is immersed in a container 55 containing the dilution 54 to be printed. When the layered cotton sheets pass between the pair of printing rollers 50, the mesh-type separating net 11 is printed onto a surface of the layered cotton sheets. The printed separating net 11 is dried and solidified. In the figure, the printing of the cotton sheets is illustrated to be achieved only by the lower printing roller 50. If desired, the dilution 54 to be printed may be also applied to an outer surface of the upper printing roller 50.

That is, according to the intended use, the separating net 11 is formed either on one surface or on both surfaces of the layered cotton sheets.

After the layered cotton sheets are embossed, and the separating net is formed on a surface of the layered cotton sheets, the layered cotton sheets are sectioned into a desired shape and size by a cutter 70 to generate a mesh cotton.

Figure 7:
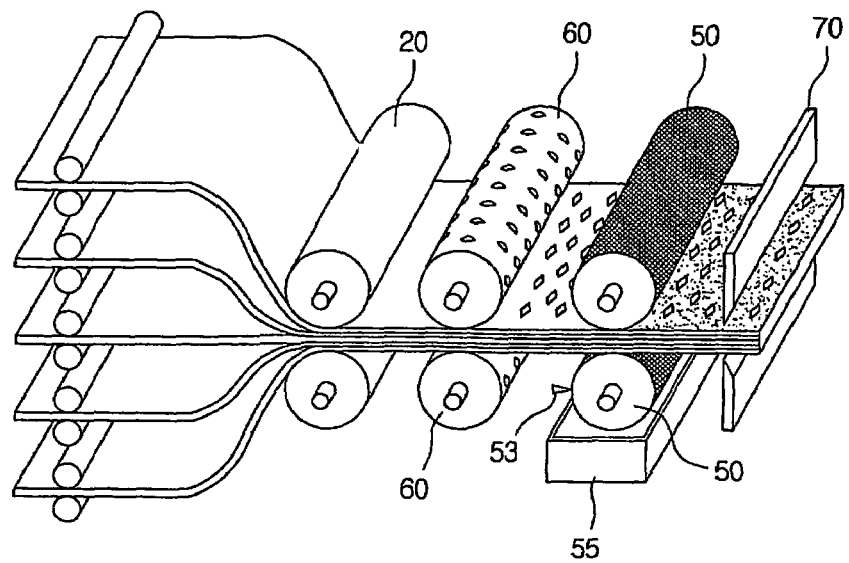
FIG. 7 is a view for describing another embodiment of the process of FIG. 4.
Figure 8:
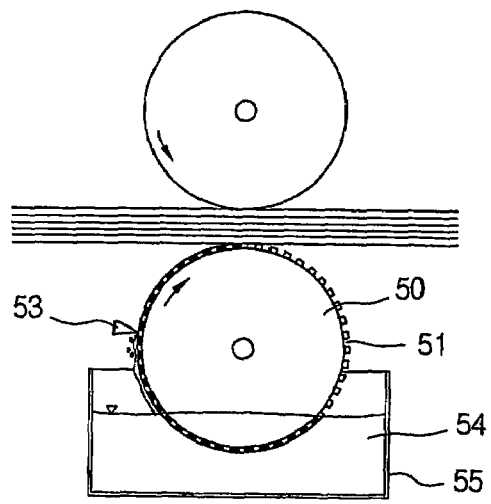
FIG. 8 shows the printing step of FIG. 5.
Figure 8:
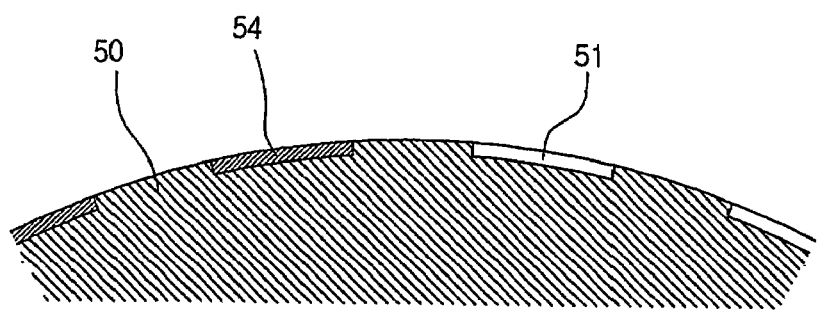
Figure 9:
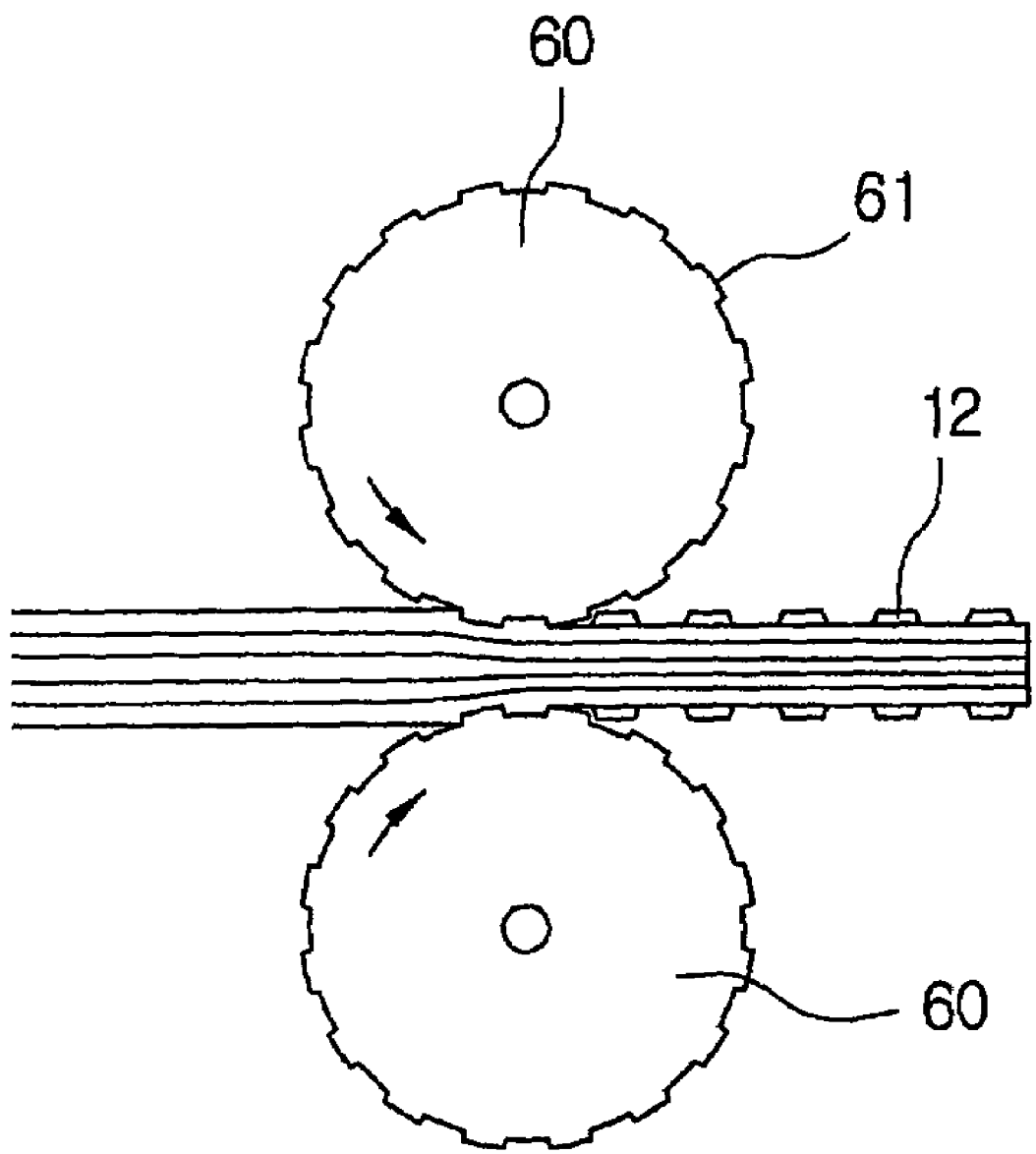
FIG. 9 shows the embossing step of FIG. 4.

FIG. 7 shows another embodiment of the layering and adhering of cotton sheets. The cotton sheets are homogeneously mixed with a viscose short staple fiber, multi-layered, and compressed using a roller 20. This embodiment simplifies the process including spraying an adhesive, absorbing the adhesive passed through the cotton sheets and drying the adhesive sprayed on the cotton sheets. Preferably, the viscose short staple fiber is coated with an adhesive to effectively adhere the cotton sheets to each other.

INDUSTRIAL APPLICABILITY

As described hereinbefore, the mesh cotton with a separating net on a surface thereof according to the present invention has the following advantages. Since fibers comprising the mesh cotton are tightly adhered to each other by the separating net, cotton applied to wound sites can be completely removed from the wound sites by the separating net. Also, since the layered cotton sheets are embossed, they are not easily separated from each other and maintain constant elasticity, thereby providing improved mesh cotton gauzes.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A mesh cotton with a separating net on a surface thereof, which is prepared by layering a plurality of cotton sheets and adhering the layered cotton sheets to each other, embossing an outer surface of the layered cotton sheets by heating under pressure to form embossments, and printing a mixture of ethylene copolymers on the outer surface of the layered cotton sheets in a mesh form to provide the separating net.

2. The mesh cotton as set forth in claim 1, wherein the layering and adhering of the cotton sheets is carried out by homogeneously mixing the cotton sheets with a viscose short staple fiber, multi-layering the cotton sheets and compressing the multi-layered cotton sheets using a roller.

3. The mesh cotton as set forth in claim 1, wherein the layering and adhering of the cotton sheets is carried out by layering the plurality of cotton sheets and adhering the layered cotton sheets to each other using an acryl binder.

4. The mesh cotton as set forth in claim 1, wherein the separating net is formed by applying in the mesh form a solution prepared by diluting a wax or a paraffin with the mixture of ethylene copolymers to the outer surface of the layered cotton sheets and solidifying the solution.

5. A method of manufacturing a mesh cotton with a separating net on a surface thereof, comprising: layering a plurality of cotton sheets and adhering the layered cotton sheets to each other; forming a mesh-type separating net on an outer surface of the layered adhered cotton sheets using a mixture of ethylene copolymers; embossing the outer surface of the cotton sheets by heating under pressure to form embossments; and sectioning the embossed cotton sheets into a predetermined shape with a predetermined size.

6. The method as set forth in claim 5, wherein the layering and adhering of the cotton sheets comprises: homogeneously mixing the cotton sheets with a viscose short staple fiber; multi-layering a resulting mixture; and compressing the multi-Layered mixture using a roller.

7. The method as set forth in claim 5, wherein the layering and adhering of the cotton sheets comprises: layering the plurality of cotton sheets; and adhering the layered cotton sheets to each other using an acryl binder.

8. The method as set forth in claim 5, wherein the layering and adhering of the cotton sheets comprises: layering the plurality of cotton sheets using a roller; and adhering the layered cotton sheets to each other by spraying an acryl binder onto a surface of the layered cotton sheets and absorbing the acryl binder at an opposite surface of the layered cotton sheets, wherein the layered cotton sheets are dried after the layering and adhering of the cotton sheets.

9. The method as set forth in claim 5, wherein the forming of the mesh-type separating net comprises printing the mixture of ethylene copolymers or a wax or a paraffin dissolved in the mixture of ethylene copolymers onto the outer surface of the layered adhered cotton sheets to provide the mesh-type separating net; and drying the printed separating net.

10. The method as set forth in claim 9, wherein the printing of the mesh-type separating net comprises: partially applying the mixture of ethylene copolymers, contained in a plurality of depressions-on an outer embossed surface of a printing roller with a lattice-shaped mesh structure on the outer embossed surface, to the outer surface of the layered cotton sheets.

11. The method as set forth in claim 5, wherein the embossing of the cotton sheets comprises: passing the layered cotton sheets between a pair of embossing rollers with an outer uneven surface to emboss both surfaces of the layered cotton sheets by the uneven surfaces of the embossing rollers.

12. The method as set forth in claim 5, wherein the adhering of the cotton sheets comprises: spraying an acryl binder onto both surfaces of the layered cotton sheets by turning upside down the layered cotton sheets or changing a location of a sprayer and an absorber of the acryl binder, wherein, after being adhered to each other, the layered cotton sheets are dried.

* * * * *